United States Patent [19]

Dohara et al.

[11] Patent Number: 5,055,299

[45] Date of Patent: Oct. 8, 1991

[54] INSECTICIDAL AEROSOL

[75] Inventors: Kazunobu Dohara, Sakai; Tadahiro Matsunaga, Kobe; Motomitsu Shiraishi, Amagasaki; Goro Shinjo, Toyanaka, all of Japan

[73] Assignee: Sumitomo Chemical Company, Limited, Osaka, Japan

[21] Appl. No.: 281,407

[22] Filed: Dec. 8, 1988

[30] Foreign Application Priority Data

Dec. 15, 1987 [JP] Japan .................. 62-318183

[51] Int. Cl.$^5$ .............................. A01N 25/00
[52] U.S. Cl. ..................... 424/405; 424/43; 424/44; 424/45
[58] Field of Search ............ 424/43, 45, 44, 405, 424/409, 411

[56] References Cited

U.S. PATENT DOCUMENTS

| | | | |
|---|---|---|---|
| 4,450,253 | 5/1984 | Suk | 524/378 |
| 4,518,734 | 5/1985 | Broulette | 524/378 |
| 4,604,226 | 8/1986 | Bartlett | 252/389 |

FOREIGN PATENT DOCUMENTS

| | | |
|---|---|---|
| 0006212 | 9/1980 | European Pat. Off. |
| 0032779 | 7/1981 | European Pat. Off. |
| 069906 | 1/1983 | European Pat. Off. |
| 54-095737 | 7/1979 | Japan . |
| 60-104003 | 6/1985 | Japan . |
| 60-104003 | 6/1985 | Japan . |
| 60-104004 | 6/1985 | Japan . |
| 60-104004 | 6/1985 | Japan . |
| 60-104203 | 6/1985 | Japan . |
| 61-45601 | 10/1986 | Japan . |

*Primary Examiner*—Lester L. Lee
*Assistant Examiner*—Stephen B. Maebius
*Attorney, Agent, or Firm*—Stevens, Davis, Miller & Mosher

[57] ABSTRACT

A mono-layer liquid phase type water-based insecticidal aerosol comprises (A) a base liquid for aerosol containing at least one specific pyrethroidal compound, a specific organic solvent and a buffer solution, which base liquid has a pH of from 7.0 to 9.0 and (B) dimethyl ether as a propellant. The aerosol according to the present invention has a long-term storage stability, as well as an excellent insecticidal activity and causes no degradation of the container.

5 Claims, No Drawings

INSECTICIDAL AEROSOL

The present invention relates to a mono-layer liquid phase type water-based insecticidal aerosol.

Recently, since water-based insecticidal aerosols can be averted from inflammability and toxicity to mammals, and since their manufacturing cost is relatively low, various developments have been forwarded on them.

However, most of the conventionally known water-based aerosols are the so-called two-layer liquid phase type water-based ones, that is, the liquid phase separates in two layers. Consequently, before the use of such aerosols, homogenizing the liquid phase by shaking is not avoidable.

To avoid the inconvenience, the so-called mono-layer liquid phase type water-based insecticidal aerosols have been developed. This type of aerosols can be prepared by dispersing an insecticidally active ingredient such as a pyrethroidal insecticidal compound in water with the aid of ethanol, etc. followed by blending thereto a propellant such as dimethyl ether, etc.

However, this type of insecticidal aerosols, when put to practical use, have serious problems that corrosion occurs on the inner wall of the aerosol container made of tinplate during the storage, which in turn causes the leak of the propellant gas, and that the effect of the aerosols is lowered by the decomposition of the insecticidal compound contained in the aerosols.

The present inventors have extensively studied to develop a mono-layer liquid phase type water-based insecticidal aerosol not causing such the problems, and as a result, have found that a mono-layer liquid phase type water-based insecticidal aerosol which comprises;

(A) a base liquid for aerosol containing as an insecticidally active ingredient at least one pyrethroidal compound selected from the following group I or a mixture of at least one pyrethroidal compound selected from the group I and at least one pyrethroidal compound selected from the following group II, an organic solvent selected from the following group III and a buffer for conditioning the pH of the base liquid from 7.0 to 9.0, and (B) dimethyl ether as a propellant, can be suited to this object: Group I:
3-allyl-2-methyl-4-oxocyclopent-2-enyl chrysanthemate (allethrin),
2-methyl-4-oxo-3-propargylcyclopent-2-enyl chrysanthemate,
5-propargylfurfuryl chrysanthemate (furamethrin),
α-cyano-3-phenoxybenzyl chrysanthemate,
α-phenoxybenzyl 2,2,3,3-tetramethylcyclopropanecarboxylate (fenpropathrin) and
2-(4-ethoxyphenyl)-2-methylpropyl 3-phenoxybenzyl ether (ethofenprox);
Group II:
3-phenoxybenzyl 2,2-dimethyl-3-(2,2-dichlorovinyl)cyclopropanecarboxylate (permethrin),
3-phenoxybenzyl chrysanthemate (phenothrin),
5-benzyl-3-furylmethyl chrysanthemate (resmethrin),
1-ethynyl-2-methyl-2-pentenyl chrysanthemate,
2-(4-ethoxyphenyl)-5-(4-fluoro-3-phenoxy)-phenyl-2-methylpentane and
2-[1-methyl-2-(4-phenoxyphenoxy)ethoxy]-pyridine (pyriproxyfen);
Group III:
isopropyl alcohol,
n-propyl alcohol,
ethyl alcohol,
propylene glycol,
propylene glycol methyl ether,
dipropylene glycol methyl ether,
tripropylene glycol methyl ether and acetone.

The present inventors thus attained to the present invention.

The insecticidal aerosol of the present invention can be kept in a homogeneous liquid phase without causing separation in two layers even when it is stored for a long period of time at a relatively high temperature. In addition, there is no generation of rust on the wall of the aerosol container, and the insecticidally active ingredients remain stable.

Accordingly, the insecticidal aerosol of the present invention can be used as they are and requires no previous shaking at the time of application, and also they can exhibit an excellent effect as an insecticide.

Each of the pyrethroidal compounds belonging to the foregoing groups I and II used as the insecticidally active ingredient has steric and optical isomers. And these isomers and their mixtures may be used in the present invention.

The insecticidally active ingredient is usually blended in the aerosol in an amount of 0.01 to 2% by weight, preferably 0.03 to 1% by weight based on the total weight of the aerosol.

Specific examples of the buffer solutions are:
ammonium benzoate-NaOH buffer solution,
sodium benzoate-benzoic acid buffer solution,
ammonium benzoate-ammonia buffer solution,
ammonium benzoate-benzoic acid buffer solution,
$KH_2PO_4$-NaOH buffer solution,
NaOH-sodium bimaleate buffer solution,
tris.maleate*-NaOH buffer solution and
* mixture of tris(hydroxymethyl)aminomethane and maleic acid
$Na_2Cl_3$-$NaHCO_3$ buffer solution.

The buffer solution is incorporated in the aerosol in an amount of 10 to 55% by weight, preferably from 20 to 50% by weight based on the total weight of the aerosol.

The amount of dimethyl ether, a propellant, used is usually from 10 to 80% by weight, preferably from 30 to 60% by weight based on the total weight of the aerosol.

The amount of the organic solvent used is usually from 10 to 70% by weight, preferably from 18 to 40% by weight.

In the insecticidal aerosols of the present invention, surface active agents, synergists, perfumes, fungicides, etc. may be used together if necessary.

As the synergists, conventional ones such as piperonyl butoxide, S-421, MGK-264, Synepirin, etc. may be used.

The insecticidal aerosols of the present invention maybe prepared, for example, by the following method: Prescribed amounts of the insecticidally active ingredient, organic solvents and if necesssary, surface active agents, synergists, perfumes, fungicides, etc. are mixed at room temperature or under heating and put in an aerosol container; a prescribed amount of the buffer solution having a prescribed pH value is added, and the base liquid for aerosol thus obtained is conditioned so as to have a pH in a range of from 7.0 to 9.0; and after mounting a valve portion on the aerosol container, dimethyl ether is charged into the container under pressure through the valve portion.

The present invention will be illustrated in more detail with reference to the following examples and comparative examples, but it is not limited to these examples.

In the following examples, parts mean a part by weight.

EXAMPLE 1

0.3 Part of allethrin and 24.7 parts of isopropyl alcohol were well mixed under heating and introduced into an aerosol container made of tinplate. To the mixture were added 30.0 parts of an ammonium benzoate-ammonia buffer solution, which had been prepared by adding a 29% aqueous ammonia to a 1.0% w/w aqueous ammonium benzoate solution and then conditioning the pH of the solution to 8.5. Thus, a base liquid for aerosol having a pH of 8.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed. It was found that the mixture was not recognized to be separated, remaining homogeneous and transparent. The content of allethrin in the aerosol was determined by gas chromatography under the following conditions and compared with the content which had been determined immediately after preparation of the aerosol. As a result, the percentage of the remainder of allethrin was found to be 95.0%.

The generation of rust on the wall of the aerosol container was not observed.

Apparatus: FID
Column: 2% DEGS [Chromosorb W (AW, DMCS, 100–120 mesh)]. Glass column of 1.1 m × 3 mm$\phi$ in size.
Column temperature: 190° C.
N$_2$ flow rate: 50 ml/min
Internal standard: Fluoranthene

EXAMPLE 2

An aerosol was prepared in the same manner as in Example 1 except that allethrin was replaced by (S)-2-methyl-4-oxo-3-propargylcyclopent-2-enyl (1R)-cis,-trans-chrysanthemate (prallethrin).

The insecticidal aerosol of the present invention thus prepared was stored at 45° C. for 3 months. Then the aerosol in the container was observed. It was found that the aerosol mixture was not recognized to be separated, remaining homogeneous and transparent. The content of prallethrin in the aerosol was determined by gas chromatography in the same manner as in Example 1 and compared with the content which had been determined immediately after preparation of the aerosol. As a result, the percentage of the remainder of prallethrin was found to be 96.7%. The generation of rust on the wall of the aerosol container was not observed.

EXAMPLE 3

An aerosol was prepared in the same manner as in Example 1 except that fenpropathrin was used in place of allethrin.

The insecticidal aerosol of the present invention thus obtained was stored at 45° C. for 3 months. Then the aerosol in the container was observed. It was found that the aerosol was not recognized to be separated, remaining homogeneous and transparent. The content of fenpropathrin in the aerosol was determined by gas chromatography under the following conditions and compared with the content which had been determined immediately after preparation of the aerosol. As a result, the percentage of the remainder of fenpropathrin was found to be 95.0%. The generation of rust on the wall of the aerosol container was not observed.

Apparatus: FID .
Column: 3% XE-60 [Chromosorb W (AW, DMCS, 60–80 mesh)]. Glass column of 1.1 m × 3 mm$\phi$ in size.
Column temperature: 220° C.
N$_2$ flow rate: 50 ml/min
Internal standard: Diphenyl phthalate.

EXAMPLE 4

0.3 Part of (RS)-α-cyano-3-phenoxybenzyl (1R)-cis,-trans-chrysanthemate (cyphenothrin), 0.5 part of sorbitan monolaurate and 24.2 parts of isopropyl alcohol were well mixed under heating and introduced into an aerosol container made of tinplate. To the mixture were added 30.0 parts of an ammonium benzoate-NaOH buffer solution, which had been prepared by adding a 10% w/w aqueous NaOH solution to a 1.0% w/w aqueous ammonium benzoate solution and then conditioning the pH of the solution to 8.5. Thus, a base liquid for aerosol having a pH of 8.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The content of cyphenothrin in the solution was determined by gas chromatography under the following conditions and compared with the content which had been determined immediately after preparation of the aerosol. As a result, the percentage of the remainder of cyphenothrin was found to be 98.2%.

The generation of rust on the wall of the aerosol container was not observed.

Apparatus, column and N2 flow rate: Same as in Example 1.
Column temperature: 210° C.
Internal standard: Tetramethrin .

EXAMPLE 5

An aerosol was prepared in the same manner as in Example 4 except that furamethrin was used in place of cyphenothrin.

The insecticidal aerosol of the present invention thus obtained was stored at 45° C. for 3 months. Then the aerosol solution in the container was observed. It was found that the aerosol was not recognized to be separated, remaining homogeneous and transparent. The content of furamethrin in the aerosol was determined by gas chromatography under the following conditions and compared with the content which had been determined immediately after preparation of the aerosol. As a result, the percentage of the remainder of furamethrin was found to be 92.9%. The generation of rust on the wall of the aerosol container was not observed.

Apparatus and N$_2$ flow rate: Same as in Example 1.
Column: 5% XE-60 [Uniport HP (60–80 mesh)].
Glass column of 1.1 m × 3 mm$\phi$ in size.
Column temperature: 160° C.

Internal standard: Dibutyl phthalate.

EXAMPLE 6

An aerosol was prepared in the same manner as in Example 4 except that ethofenprox was used in place of cyphenothrin.

The insecticidal aerosol of the present invention thus obtained was stored at 45° C. for 3 months. Then the aerosol in the container was observed. It was found that the aerosol was not recognized to be separated, remaining homogeneous and transparent. The content of ethofenprox in the aerosol was determined by gas chromatography under the following conditions and compared with the content which had been determined immediately after preparation of the aerosol. As a result, the percentage of the remainder of ethofenprox was found to be 93.7%. The generation of rust on the wall of the aerosol container was not observed.

Apparatus and $N_2$ flow rate: Same as in Example 1.
Column: 5% OV-101 [Uniport HP (100-120 mesh)].
Glass column of 1.1 m×3 mm$\phi$ in size.
Column temperature: 260° C.
Internal standard: Triphenyl phosphate.

COMPARATIVE EXAMPLE 1

An aerosol was prepared in the same manner as in Example 1 except that tetramethrin was used in place of allethrin.

The insecticidal aerosol thus obtained was stored at 45° C. for 1 month, and the content of tetramethrin in the aerosol was determined by gas chromatography under the following conditions and compared with the content which had been determined immediately after preparation of the aerosol. As a result, the percentage of the remainder of tetramethrin was found to be 50.1%

Apparatus, column and $N_2$ flow rate: Same as in Example 1.
Column temperature: 210° C.
Internal standard: Phenothrin.

COMPARATIVE EXAMPLE 2

An aerosol was prepared in the same manner as in Example 1 except that fenitrothion was used in place of allethrin.

The insecticidal aerosol thus obtained was stored at 45° C. for 3 months, and the content of fenitrothion in the aerosol was determined by gas chromatography under the following conditions and compared with the content which had been determined immediately after preparation of the aerosol. As a result, the percentage of the remainder of fenitrothion was found to be 50.1%.

Apparatus column and $N_2$ flow rate: Same as in Example 1.
Column temperature: 195° C.
Internal standard: Cyanophos.

COMPARATIVE EXAMPLE 3

An aerosol was prepared in the same manner as in Example 4 except that deltamethrin was used in place of cyphenothrin.

The insecticidal aerosol thus obtained was stored at 45° C. for 3 months, and the content of deltamethrin in the aerosol was determined by gas chromatography under the following conditions and compared with the content which had been determined immediately after preparation of the aerosol. As a result, the percentage of the remainder of deltamethrin was found to be 44.3%.

Apparatus and $N_2$ flow rate: Same as in Example 1.
Column: 3% OV-101 [Sumikasorb HP (100 120 mesh)].
Glass column of 1.1 m×3 mm$\phi$ in size.
Column temperature: 230° C.
Internal standard: Phenylbiphenylyl-1,3,4-oxadiazole

COMPARATIVE EXAMPLE 4

An aerosol was prepared in the same manner as in Example 4 except that propoxur was used in place of cyphenothrin.

The insecticidal aerosol thus obtained was stored at 45° C. for 3 months, and the content of propoxur in the aerosol was determined by gas chromatography under the following conditions and compared with the content which had been determined immediately after preparation of the aerosol. As a result, the percentage of the remainder of propoxur was found to be 69.7%.

Apparatus and $N_2$ flow rate: Same as in Example 1.
Column: 2% XE-60 [Chromosorb W (HP, 100-120 mesh)]. Glass column of 1.1 m ×3 mm$\phi$ in size.
Column temperature: 170° C.
Internal standard: n-Butyl sebacate

COMPARATIVE EXAMPLE 5

An aerosol was prepared in the same manner as in Example 4 except that deionized water was used in place of the buffer solution.

On storing the insecticidal aerosol thus obtained at 45° C. for 3 months, the generation of rust on the wall of the aerosol container was so remarkable that pin holes were bored through the wall.

EXAMPLE 7

0.4 Part of allethrin, 0.1 part of resmethrin, 0.5 part of sorbitan monolaurate and 19.0 parts of isopropyl alcohol were well mixed under heating and introduced into an aerosol container made of tinplate. To the mixture were added 20.0 parts of an ammonium benzoate-NaOH buffer solution, which had been prepared by adding a 10% w/w aqueous NaOH solution to a 1.0% w/w aqueous ammonium benzoate solution and then conditioning the pH of the solution to 9.5. Thus, a base liquid for aerosol having a pH of 9.0 was prepared. Thereafter, a valve portion was mounted on the aerosol container, and 60.0 parts of dimethyl ether were charged into the container under pressure through the valve portion.

The insecticidal aerosol of the present invention thus prepared was stored at 45° C. for 3 months, Then the aerosol in the container was observed. It was found that the aerosol was not recognized to be separated, remaining homogeneous and transparent. The contents of allethrin and resmethrin in the aerosol were determined by gas chromatography under the following conditions and compared with the contents which had been determined immediately after preparation of the aerosol. As a result, the percentages of the remainders of allethrin and resmethrin were found to be 94.5% and 99.8%, respectively.

The generation of rust on the wall of the aerosol container was not observed.

(1) Allethrin:
Apparatus, column and $N_2$ flow rate: Same as in Example 1.
Column temperature: 210° C.
Internal standard: Phenothrin.
(2) Resmethrin:
Apparatus, column and $N_2$ flow rate: Same as in Example 1.

Column temperature: 210° C.
Internal standard: Phenothrin

EXAMPLE 8

0.1 Part of prallethrin, 0.1 part of cyphenothrin and 39.8 parts of isopropyl alcohol were well mixed under heating and introduced into an aerosol container made of tinplate. To the mixture were added 20.0 parts of an ammonium benzoate-ammonia buffer solution, which had been prepared by adding a 29% aqueous ammonia to a 1.0% w/w aqueous ammonium benzoate solution and then conditioning the pH of the mixed solution to 8.5. Thus, a base liquid for aerosol having a pH of 8.0 was prepared. Thereafter, a valve portion was mounted on the aerosol container, and 40.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The contents of prallethrin and cyphenothrin in the aerosol were determined by gas chromatography in the same manner as in Example 4 and compared with the contents which had been determined immediately after preparation of the aerosol. As a result, the percentages of the remainders of prallethrin and cyphenothrin were found to be 94.3% and 95.2%, respectively.

The generation of rust on the wall of the aerosol container was not observed.

EXAMPLE 9

0.4 Part of allethrin, 0.1 part of permethrin and 19.5 parts of isopropyl alcohol were well mixed under heating and charged into an aerosol container made of tinplate. To the mixture were added 50.0 parts of an ammonium benzoate-ammonia buffer solution, which had been prepared by adding a 29% aqueous ammonia to a 1.0% w/w aqueous ammonium benzoate solution and then conditioning the pH of the mixed solution to 8.5. Thus, a base liquid for aerosol having a pH of 8.0 was prepared. Thereafter, a valve portion was mounted on the aerosol container, and 30.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The contents of allethrin and permethrin in the aerosol were determined by gas chromatography under the following conditions and compared with the contents which had been determined immediately after preparation of the aerosol. As a result, the percentages of the remainders of allethrin and permethrin were found to be 94.1% and 98.0%, respectively.

The generation of rust on the wall of the aerosol container was not observed.

(1) Allethrin:
Apparatus, column, $N_2$ flow rate and internal standard: Same as in Example 1.
Column temperature: 210° C.
(2) Permethrin:
Apparatus, column and $N_2$ flow rate: Same as in Example 1.
Column temperature: 210° C.
Internal standard: tetramethrin.

EXAMPLE 10

0.3 Part of furamethrin, 0.1 part of phenothrin, 0.5 part of sorbitan monolaurate and 39.1 parts of isopropyl alcohol were well mixed under heating and introduced into an aerosol container made of tinplate. To the mixture were added 30.0 parts of an ammonium benzoate-ammonia buffer solution, which had been prepared by adding a 29% aqueous ammonia to a 1.0% w/w aqueous ammonium benzoate solution and then conditioning the pH of the solution to 8.5. Thus, a base liquid for aerosol having a pH of 8.0 was prepared. Thereafter, a valve portion was mounted on the aerosol container, and 30.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The contents of furamethrin and phenothrin in the aerosol were determined by gas chromatography under the following conditions and compared with the contents which had been determined immediately after preparation of the aerosol. As a result, the percentages of the remainders of furamethrin and phenothrin were found to be 93.3% and 94.0%, respectively.

The generation of rust on the wall of the aerosol container was not observed.

(1) Furamethrin:
Apparatus, column, column temperature, $N_2$ flow rate and internal standard: Same as in Example 5.
(2) Phenothrin:
Apparatus, column and $N_2$ flow rate: Same as in Example 1.
Column temperature: 210° C.
Internal standard: Tetramethrin

COMPARATIVE EXAMPLE 6

An aerosol was prepared in the same manner as in Example 8 except that an ammonium benzoate-ammonia buffer solution having a pH of 10.5 was used, and that the pH of the base liquid for aerosol was conditioned to 10.0.

The insecticidal aerosol thus obtained was stored at 45° C. for 3 months, and the contents of prallethrin and cyphenothrin in the aerosol were determined by gas chromatography in the same manner as in Example 8 and compared with the contents which had been determined immediately after preparation of the aerosol. As a result, the percentages of the remainders of prallethrin and cyphenothrin were found to be 38.7% and 46.7%, respectively.

COMPARATIVE EXAMPLE 7

An aerosol was prepared in the same manner as in Example 8 except that an ammonium benzoate-ammonia buffer solution having a pH of 4.5 was used, and that the pH of the base liquid for aerosol was conditioned to 6.0.

On storing the insecticidal aerosol thus obtained at 45° C. for 3 months, the generation of rust on the wall of the aerosol container was so remarkable that pin holes were bored through the wall.

EXAMPLE 11

0.6 Part of allethrin, 0.2 part of phenothrin and 24.2 parts of isopropyl alcohol were well mixed under heating and introduced into an aerosol container made of tinplate. To the mixture were added 30.0 parts of an ammonium benzoate-ammonia buffer solution, which had been prepared by adding a 29% aqueous ammonia to a 1.0% w/w aqueous ammonium benzoate solution and then conditioning the pH of the solution to 9.5. Thus, a base liquid for aerosol having a pH of 9.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The contents of allethrin and phenothrin in the aerosol were determined by gas chromatography under the following conditions and compared with the contents which had been determined immediately after preparation of the aerosol. As a result, the percentages of the remainders of allethrin and phenothrin were found to be 95.6% and 97.8%, respectively.

The generation of rust on the wall of the aerosol container was not observed.

(1) Allethrin:

Apparatus, column, $N_2$ flow rate and internal standard: Same as in Example 1.

Column temperature: 200° C.

(2) Phenothrin:

25 Apparatus, column, $N_2$ flow rate and internal standard: Same as in Example 1.

Column temperature: 200° C.

EXAMPLE 12

0.3 Part of allethrin and 24.7 parts of isopropyl alcohol were well mixed under heating and introduced into an aerosol container made of tinplate. To the mixture were added 30.0 parts of an ammonium benzoate-ammonia buffer solution, which had been prepared by adding a 29% aqueous ammonia to a 1.0% w/w aqueous ammonium benzoate solution and then conditioning the pH of the solution to 9.5. Thus, a base liquid for aerosol having a pH of 9.0 was prepared. Thereafter, a valve portion was mounted on the aerosol container, and 45.0 parts of dimethyl ether were charged into the container under pressure through the valve portion.

The insecticidal aerosol of the present invention thus prepared was stored at 45° C. for 3 months. Then the aerosol in the container was observed. It was found that the aerosol was not recognized to be separated, remaining homogeneous and transparent. The content of allethrin in the solution was determined by gas chromatography in the same manner as in Example 1 and compared with the content which had been determined immediately after preparation of the aerosol. As a result, the percentage of the remainder of allethrin was found to be 92 3%.

The generation of rust on the wall of the aerosol container was not observed.

EXAMPLE 13

An aerosol was prepared in the same manner as in Example 12 except that ethyl alcohol was used in place of isopropyl alcohol.

The insecticidal aerosol of the present invention thus prepared was stored at 45° C. for 3 months. Then the aerosol in the container was observed. It was found that the aerosol was not recognized to be separated, remaining homogeneous and transparent. The content of allethrin in the aerosol was determined by gas chromatography in the same manner as in Example 1 and compared with the content which had been determined immediately after preparation of the aerosol. As a result, the percentage of the remainder of allethrin was found to be 93.3%.

The generation of rust on the wall of the aerosol container was not observed.

EXAMPLE 14

An aerosol was prepared in the same manner as in Example 12 except that propylene glycol was used in place of isopropyl alcohol.

The insecticidal aerosol of the present invention thus prepared was stored at 45° C. for 3 months. Then the aerosol in the container was observed. It was found that the aerosol was not recognized to be separated, remaining homogeneous and transparent. The content of allethrin in the aerosol was determined by gas chromatography in the same manner as in Example 1 and compared with the content which had been determined immediately after preparation of the aerosol. As a result, the percentage of the remainder of allethrin was found to be 90 3%.

The generation of rust on the wall of the aerosol container was not observed.

EXAMPLE 15

An aerosol was prepared in the same manner as in Example 12 except that tripropylene glycol methyl ether was used in place of isopropyl alcohol.

The insecticidal aerosol of the present invention thus prepared was stored at 45° C. for 3 months. Then the aerosol in the container was observed. It was found that the aerosol was not recognized to be separated, remaining homogeneous and transparent. The content of allethrin in the aerosol was determined by gas chromatography in the same manner as in Example 1 and compared with the content which had been determined immediately after preparation of the aerosol. As a result, the percentage of the remainder of allethrin was found to be 93.8%.

The generation of rust on the wall of the aerosol container was not observed.

COMPARATIVE EXAMPLE 8

An aerosol was prepared in the same manner as in Example 12 except that hexylene glycol was used in place of isopropyl alcohol.

The insecticidal aerosol thus obtained was stored at 45° C. for 3 months. Then the content of allethrin in the aerosol was determined by gas chromatography as in Example 1 and compared with the content which had been determined immediately after preparation of the aerosol. As a result, the percentage of the remainder of allethrin was found to be 79.8%.

COMPARATIVE EXAMPLE 9

An aerosol was prepared in the same manner as in Example 12 except that methyl cellosolve was used in place of isopropyl alcohol.

The insecticidal aerosol thus obtained was stored at 45° C. for 3 months. Then the content of allethrin in the aerosol was determined by gas chromatography in the same manner as in Example 1 and compared with the content which had been determined immediately after preparation of the aerosol. As a result, the percentage of the remainder of allethrin was found to be 76.3%.

What is claimed is:

1. A mono-layer liquid phase type water-based insecticidal aerosol which comprises
   (A) a base liquid for aerosol containing as an insecticidally active ingredient at least one pyrethroidal compound selected from the following group I or a mixture of at least one pyrethroidal compound of the group I and at least one pyrethroidal compound selected from the following group II, an organic solvent selected from the following group III and a buffer solution for conditioning the pH of the base liquid from 7.0 to 9.0, and
   (B) dimethyl ether as a propellant. Group I:
      3-allyl-2-methyl-4-oxocyclopent-2-enyl chrysanthemate (allethrin),
      2-methyl-4-oxo-3-propargylcyclopent-2-enyl chrysanthemate,
      5-propargylfurfuryl chrysanthemate (furamethrin),
      α-cyano-3-phenoxybenzyl chrysanthemate,
      α-cyano-3-phenoxybenzyl 2,2,3,3-tetramethylcyclopropanecarboxylate (fenpropathrin) and
      2-(4-ethoxyphenyl)-2-methylpropyl 3-phenoxybenzyl ether (ethofenprox); Group II:
      3-phenoxybenzyl 2,2-dimethyl-3-(2,2-dichlorovinyl)cyclopropanecarboxylate (permethrin),
      3-phenoxybenzyl chrysanthemate (phenothrin),
      5-benzyl-3-furylmethyl chrysanthemate (resmethrin),
      1-ethynyl-2-methyl-2-pentenyl chrysanthemate,
      2-(4-ethoxyphenyl)-5-(4-fluoro-3-phenoxy)-phenyl-2-methylpentane and
      2-[1-methyl-2-(4-phenoxyphenoxy)ethoxy]-pyridine (pyriproxyfen);
   Group III:
      isopropyl alcohol,
      n-propyl alcohol,
      ethyl alcohol,
      propylene glycol,
      propylene glycol methyl ether,
      dipropylene glycol methyl ether,
      tripropylene glycol methyl ether and acetone.

2. An aerosol according to claim 1, wherein dimethyl ether is blended in the aerosol as a propellant in an amount of 10 to 80% by weight based on the total weight of the aerosol.

3. An aerosol according to claim 1, which comprises an organic solvent selected from the group consisting of isopropyl alcohol, n-propyl alcohol, ethyl alcohol, propylene glycol, propylene glycol methyl ether, dipropylene glycol methyl ether, tripropylene glycol methyl ether and acetone in an amount of from 10 to 70% by weight based on the total weight of the aerosol.

4. An aerosol according to claim 1, which comprises the buffer solution in an amount of from 10 to 55% by weight based on the total weight of the aerosol.

5. An aerosol according to claim 1, which comprises said insecticidally active ingredient in an amount of from 0.01 to 2% by weight based on the total weight of the aerosol.

* * * * *